United States Patent [19]

Wallace et al.

[11] 4,215,224

[45] Jul. 29, 1980

[54] REMOVAL OF DISSOLVED DISODIUM TEREPHTHALATE FROM AQUEOUS SOLUTION ALSO CONTAINING SODIUM HYDROXIDE

[75] Inventors: Franklin D. Wallace; John C. Carr, both of Decatur, Ala.

[73] Assignee: Standard Oil Company (Indiana), Chicago, Ill.

[21] Appl. No.: 968,507

[22] Filed: Dec. 11, 1978

[51] Int. Cl.$^2$ .............................................. C07C 51/42
[52] U.S. Cl. .................................. 562/485; 423/183; 423/641; 562/486
[58] Field of Search ...................... 423/182, 183, 641; 562/485, 486

[56] References Cited

U.S. PATENT DOCUMENTS

| 2,697,723 | 12/1954 | Carlston | 562/485 |
| 2,719,109 | 9/1955 | Harper | 423/183 |

*Primary Examiner*—Alan Siegel
*Attorney, Agent, or Firm*—Fred R. Ahlers; William T. McClain; William H. Magidson

[57] ABSTRACT

This invention relates to the removal of substantially all of the disodium terephthalate ($Na_2TA$) dissolved in a dilute aqueous solution of sodium hydroxide. More particularly this invention pertains to the recovery for reuse of an aqueous solution containing 5 weight percent sodium hydroxide from an aqueous solution containing, on a weight basis, from 5 to 5.25 percent $Na_2TA$ and 2.5 to 3.0 percent sodium hydroxide.

6 Claims, No Drawings

REMOVAL OF DISSOLVED DISODIUM TEREPHTHALATE FROM AQUEOUS SOLUTION ALSO CONTAINING SODIUM HYDROXIDE

BACKGROUND ART

No publicly available disclosure has been found which describes the removal of substantially all of $Na_2TA$ from a dilute aqueous solution of sodium hydroxide as a step in the recovery of an aqueous solution of sodium hydroxide.

We are, however aware of the disclosure of U.S. Pat. No. 2,697,723 which is concerned with the separation of isophthalic acid and terephthalic acid mixtures by converting such phthalic acid mixture to its disodium salt by dissolving the mixture in aqueous sodium hydroxide. The mixed disodium salts are separated by dissolving the mixture in water and either evaporating solvent water until there remains only sufficient water to dissolve disodium isophthalate (1.7 part by weight water per 1.0 part by weight disodium isophthalate) or saturating the water of the solution with sodium chloride. Both of such steps precipitate least soluble disodium terephthalate substantially completely by making use of precipitation by the common ion effect. Said patent discloses that disodium terephthalate is soluble at 25° C. in water to the extent of 14 weight percent but is soluble to the extent of less than 0.2 weight percent at 25° C. in either saturated aqueous sodium chloride or saturated aqueous disodium isophthalate solutions (37 weight percent in water at 25° C.).

From such facts a skilled chemist would not be led to use 12 to 14 weight percent sodium hydroxide to precipitate disodium terephthalate from an aqueous solution thereof. Further, the skilled chemist could not determine from the low (less than 0.2 weight percent) disodium terephthalate concentration in water saturated with sodium chloride, the required sodium ion concentration in gram atoms of sodium per liter of aqueous solution to be provided by sodium hydroxide to precipitate substantially all the disodium terephthalate dissolved in water based on the common ion effect of exceeding the solubility product.

The solubility product is applicable to dilute solutions in pure water. This invention uses relatively concentrated salt solutions. In concentrated solutions the nature of the solvent has been changed. The addition of an electrolyte to a salt solution usually increases the solubility of the salt based on the interionic attraction theory. There are deviations and the addition of some electrolytes will decrease the solubility of the salt. This patent deals with the solubility of sodium terephthalate in sodium hydroxide. The skilled chemist could not predict that sodium terephthalate would be insoluble in 14% sodium hydroxide (8% sodium) from the data that sodium terephthalate is 0.2% soluble in saturated sodium chloride (36% NaCl ≡ 14.3% sodium).

The problem related to such removal of $Na_2TA$ from a dilute aqueous solution of sodium hydroxide comes from the manufacture of terephthalic acid one of the reactants used in the manufacture of terephthalate polyesters suitable for film, fiber or filament production.

Terephthalic acid is produced, for the most part, by the catalytic liquid phase air oxidation of p-xylene in a stirred-tank type oxidation vessel, at an elevated temperature (e.g., 180° C. to 235° C.) and an elevated pressure (e.g., a gauge pressure of from 15 up to 30 $kg/cm^2$). Most of the terephthalic acid (TA) produced from such oxidation precipitates during the oxidation so that the fluid effluent from such reaction is a suspension of solid TA in acetic mother liquor. Some of the precipitated TA adheres to the inner wall of the reaction vessel even in the best design so far devised for such stirred-tank type oxidation vessel.

The fluid oxidation effluent flows from the oxidation vessel at said elevated temperature and pressure through a valved transfer line into a multi-step (generally 2 or 3 step) cooling and decompressing system which precipitates more TA. The resulting slurry is then fed to a solid-liquid separation step (e.g., centrifugation or filtration) to separate and recover TA from the acetic acid mother liquor. TA adheres to the inner walls of the transfer lines (pipe and fittings) the cooling and decompressing vessels and the solid-liquid separation apparatus as well as acetic acid mother liquor transfer lines and receiving vessels.

The acetic acid mother liquor is subjected to indirect heat exchange in either its return to the oxidation step or to distillative recovery of acetic acid from water and oxygen-containing aromatic compounds produced during the oxidation. Here again terephthalic acid adheres to inner walls of transfer lines and heat exchange surfaces.

TA so produced may require further purification. This can be done by recrystallization from water or acetic acid solution or a combination thereof with a catalytic hydrogen treatment of the water or acetic acid solution at elevated temperature and pressure (e.g., 260° C. and 73 $kg/cm^2$ gauge pressures). Here also TA can adhere to inner walls of transfer, reaction and crystallization vessels.

In commercial operations wherein the foregoing process steps are conducted continuously, it is necessary to shutdown one or more of the steps and clean the adhering TA from the inner walls of transfer lines, heat exchangers and process vessels. Such cleaning of adhering TA can conveniently be accomplished by contacting said surfaces with hot (e.g., 100° C.) dilute aqueous solution of sodium hydroxide which dissolves the adhering TA as $Na_2TA$.

While water at convenient, feasibly obtained temperatures, in commercial chemical operations can hold more than five to six weight percent $Na_2TA$ in solution, it is better practice for the washing of adhering TA from transferring, heating and processing apparatus to limit the dissolved $Na_2TA$ to 5 to 6 weight percent in the resultant aqueous wash liquor solution because such concentration even at 20° C. will retain the $Na_2TA$ in solution and prevent redeposition of $Na_2TA$ on surfaces being cleaned. Such resultant aqueous wash liquor solution having a 5 to 6 weight percent $Na_2TA$ content rapidly and readily forms from an aqueous wash solution containing 5 to 6 weight percent sodium hydroxide. From use of such caustic solution its sodium hydroxide content need not be depleted. Rather the 5 weight percent caustic solution should be used in sufficient amount to retain unused sodium hydroxide in the wash liquor solution at a 2 to 3 weight percent concentration.

Such wash liquor from a TA manufacturing plant can be discard into an aerobic-anaerobic waste treatment system wherein micro-organisms digest discarded organic and inorganic compounds and leave a non-polluting sludge and a non-polluting aqueous stream which readily aerates and holds dissolved oxygen without consuming dissolved oxygen.

DESCRIPTION OF THE INVENTION

The present invention comprises: (a) contacting at a temperature of from 20° C. up to 100° C. an aqueous solution containing 5 to 6 weight percent sodium hydroxide the inner wall surfaces of elements of apparatus used in production of terephthalic acid by the steps from the oxidation of p-xylene with air in the presence of a liquid phase of acetic acid containing dissolved components of catalysis through separation of solid terephthalic acid from acetic acid mother liquor and drying the separated terephthalic acid wherein said contacting the amount of the sodium hydroxide solution used dissolves as the disodium salt substantially all of the terephthalic acid adhering to said walls and leaves unreacted sodium hydroxide in an amount of from 2 to 3 weight percent of the solution; (b) adding sodium hydroxide to the solution of disodium terephthalate and unreacted sodium hydroxide to increase its concentration to the range of from 12 up to 14 weight percent whereby from 94 percent up to substantially all of the dissolved disodium terephthalate precipitates; (c) separating the aqueous solution containing 12 to 14 weight percent sodium hydroxide from precipitated disodium terephthalate; (d) dividing the separated solution of 12 to 14% sodium hydroxide into a major portion of more than 65 percent and a minor portion of less than 35% of the separated solution; (e) diluting said minor portion with water to a sodium hydroxide content of 5 to 6 weight percent for reuse in step (a); and (f) concentrating said major portion of the 12–14% sodium hydroxide solution to 50 weight percent sodium hydroxide for use in step (b). Optionally the disodium terephthalate precipitate is incinerated and the sodium content of the incineration ash as sodium hydroxide to the major portion of the separated solution either by extracting such ash with said major portion of the separated solution or by extracting said ash with water and combining the aqueous extract solution with the major portion of the separated solution and the resulting combined solution is concentrated to 50% NaOH content.

The best mode for practicing the present invention was devised from the information obtained in the following manner whereby the solubility of disodium terephthalate in aqueous sodium hydroxide solutions of various concentrations was determined.

There are combined and stirred five grams of terephthalic acid and 100 grams of aqueous sodium hydroxide solution containing five weight percent NaOH. The resulting solution contains 6.3253 grams (0.03 gram mole) disodium terephthalate and 2.6 grams sodium hydroxide. To the resulting solution there is added with stirring an aqueous solution containing 50 weight percent sodium hydroxide. After the addition of ten milliliters of the 50% NaOH, the total NaOH present was 10.226 grams in 105 milliliters of solution which caused a precipitate to form. The precipitate is found to be 2.2 grams disodium terephthalate. As the sodium hydroxide content is increased by addition of 50% sodium hydroxide, it is determined that 0.3253 grams of disodium terephthalate (6 grams precipitated) remains in solution at a sodium hydroxide concentration of 11.5 weight percent. Finally at a sodium hydroxide content of 13.8% all the disodium terephthalate had precipitated.

The following process illustrates the best mode presently contemplated for the practice of this invention.

The elements of apparatus used in the production of terephthalic acid are washed at a temperature of 25° C. with an aqueous solution (1.0538 grams/ml) containing five weight percent NaOH in the amount of 200 grams of solution per 10 grams of adhering terephthalic acid. The amount of adhering terephthalic acid was known from historical operation of the process.

The resulting wash solution was cooled to 25° C. and for each 210 gram aliquot thereof which contained 12.65 grams of disodium terephthalate and 5.2 grams sodium hydroxide there are added 67.2 grams of aqueous solution (1.5253 grams/ml) containing 50 weight percent NaOH to increase the NaOH concentration to 14 weight percent. All the disodium terephthalate precipitates from solution as a small particle size, readily filterable solids. The precipitate is recovered by filtration and then incinerated. The filtrate is divided into a major portion comprising 73.6 weight percent and a minor portion comprising 26.4 weight percent which is diluted with water to a NaOH content of 5 weight percent and then recycled to the next washing of terephthalic acid production apparatus.

The 73.6% major portion of the 14% NaOH solution separated from the disodium terephthalate precipitates is heated to evaporate 83.7% of the water to produce a 50 weight percent NaOH solution in water. By increasing the NaOH concentration of the extract solution plus 50% NaOH solution to 14% NaOH rather than 12% NaOH avoids a second precipitation of disodium terephthalate during evaporation.

Optionally the incineration's ash is extracted with 100° C. water to recover the sodium content of the ash as a solution of sodium hydroxide. The ash extract solution is combined with the 73.6 percent major portion of the 14 weight percent NaOH from which disodium terephthalate had been precipitated. The combined solution is heated to evaporate water until the concentrated solution contains 50 weight percent NaOH.

The invention claimed is:

1. A method for the recovery of sodium hydroxide for reuse in removing terephthalic acid adhering to inner walls of elements of apparatus used in the production of terephthalic acid including catalytic liquid phase air oxidation of p-xylene through drying of the terephthalic acid product wherein such removal of adhering terephthalic acid is accomplished by washing the walls with an aqueous solution containing 5 to 6 weight percent sodium hydroxide used in an amount to dissolve terephthalic acid in the wash liquor as its disodium salt in a 2 to 3 weight percent concentration and which leaves some sodium hydroxide unreacted; which sodium hydroxide recovery method comprises adding sodium hydroxide to the wash liquor to increase its sodium hydroxide content to 12 to 14 weight percent whereat from 94 percent up to substantially all of the disodium terephthalate precipitates, separating the aqueous solution containing 12 to 14% sodium hydroxide from the precipitate, dividing the separated solution containing 12 to 14 weight percent sodium hydroxide into a major portion comprising more than 65% of such separated solution and a minor portion comprising less than 35% of such separated solution, diluting the minor portion of such separated solution with water to a sodium hydroxide content in the range of from 5 up to 6 weight percent, recycling said diluted minor portion of such separated solution to the washing of terephthalic acid adhering on inner walls of production apparatus, concentrating the major portion of such separated solution of 12 to 14 percent sodium hydroxide to increase its concentration to 50 weight percent.

2. The method of claim 1 wherein the wash liquor is combined with an aqueous solution containing 50 weight percent sodium hydroxide until its content in the resulting aqueous solution is 14 weight percent.

3. The method of claim 1 wherein the disodium terephthalate precipitate is incinerated and the sodium content of the ash from incineration is added as sodium hydroxide to such major portion of the separated solution containing 12 to 14 weight percent sodium hydroxide before concentration of said solution to 50 weight percent sodium hydroxide.

4. The method of claim 3 wherein the disodium terephthalate precipitate is incinerated and the sodium content of the incineration's ash is added as sodium hydroxide to such major portion of the separated solution containing 12 to 14 weight percent sodium hydroxide before concentration of said solution to 50 weight percent sodium hydroxide.

5. The method of claim 4 wherein the addition of the ash's sodium content to such major portion of the separated solution is accomplished by leaching said ash with water and adding the resulting extract solution to such major portion of the separated solution.

6. The method of claim 4 wherein the addition of the ash's sodium content to such major portion of the separated solution is accomplished by extracting the ash with such major portion of the separated solution or a fraction of such major portion and combining the resulting extract solution with the remainder of such major portion of the separated solution.

* * * * *